United States Patent [19]

Martin et al.

[11] Patent Number: 4,737,323

[45] Date of Patent: Apr. 12, 1988

[54] LIPOSOME EXTRUSION METHOD

[75] Inventors: Francis J. Martin, San Francisco; Jacqueline K. Morano, Mountain View, both of Calif.

[73] Assignee: Liposome Technology, Inc., Menlo Park, Calif.

[21] Appl. No.: 829,710

[22] Filed: Feb. 13, 1986

[51] Int. Cl.$^4$ .......................... A61K 9/52; B01J 13/02
[52] U.S. Cl. .................... 264/4.3; 210/500.23; 210/500.26; 424/420; 424/450; 428/402.2; 436/829; 514/34
[58] Field of Search ..................... 264/4.3; 428/402.2; 424/19, 38, 420, 450; 436/829; 210/500.23, 500.26

[56] References Cited

U.S. PATENT DOCUMENTS

| | | | |
|---|---|---|---|
| 4,241,046 | 12/1980 | Papahadjopoulos et al. | 424/19 |
| 4,372,949 | 2/1983 | Kodama et al. | 424/38 X |
| 4,394,372 | 7/1983 | Taylor | 514/78 G X |
| 4,429,008 | 1/1984 | Martin et al. | 424/38 X |
| 4,460,577 | 7/1984 | Moro et al. | 424/38 |
| 4,508,703 | 4/1985 | Redziniak et al. | 264/4.6 X |
| 4,529,561 | 7/1985 | Hunt et al. | 264/4.1 X |

FOREIGN PATENT DOCUMENTS 2549736 2/1985 France ........................... 210/500.26

OTHER PUBLICATIONS

Norton Publication, for Ceraflo TM Asymmetric Ceramic Microfilters, "A New Breakthrough in Separation Technology", Norton Company, 1984, High Performance Ceramics, 1 New Bond Str., Worcester, MA 01606, Printed in U.S.A., (total 6 pp.), Membrane Filtration Publication, for Uni-Pore Membrane Filters, (total 1 p.), p. 80, Feb. 1980.
Chemistry and Physics of Lipids 12, (1973), 75-95 pp., North-Holland Publ. Co., "Studies on Phosphatidylcholine Model Membranes I., Size-Heterogeneity Effect on Permeability Mesurement, by S. E. Schullery & J. P. Garzaniti, Chem. Dept. Eastern Mich. U., U.S.A.

Primary Examiner—Richard D. Lovering
Attorney, Agent, or Firm—Ciotti & Murashige, Irell & Manella

[57] ABSTRACT

A suspension of liposomes whose sizes are predominantly greater than about 1 micron is passed through an asymmetric ceramic filter whose inner-surface pore size is about 1 micron. The processed liposomes have a selected average size of about 0.4 microns or less, depending on the number of filter cycles, and a narrow distribution.

7 Claims, 1 Drawing Sheet

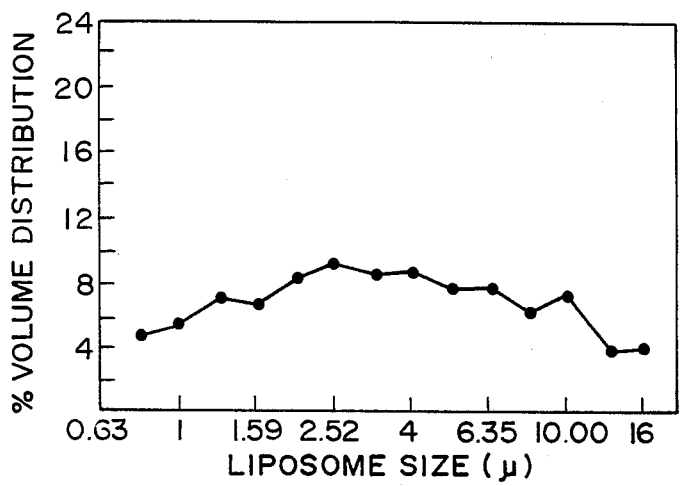
FIG. 1
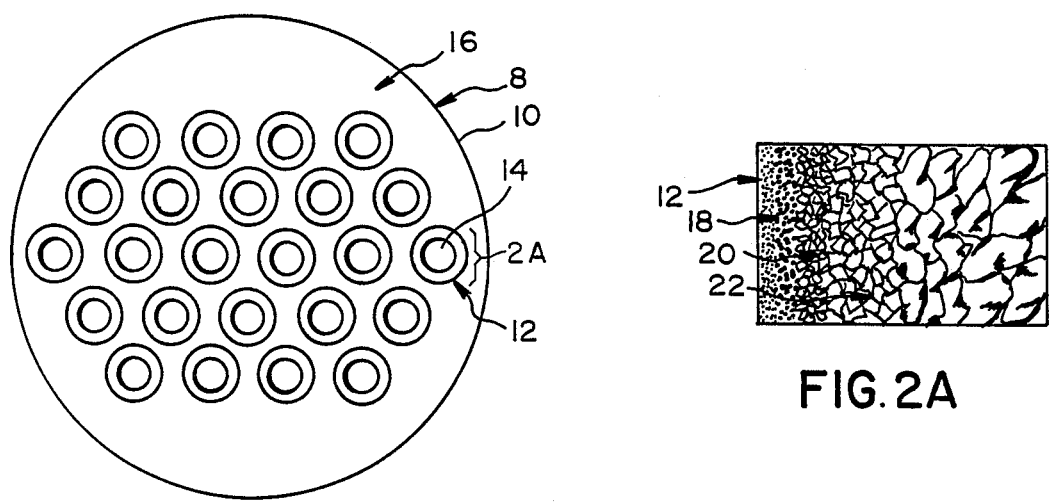
FIG. 2
FIG. 2A
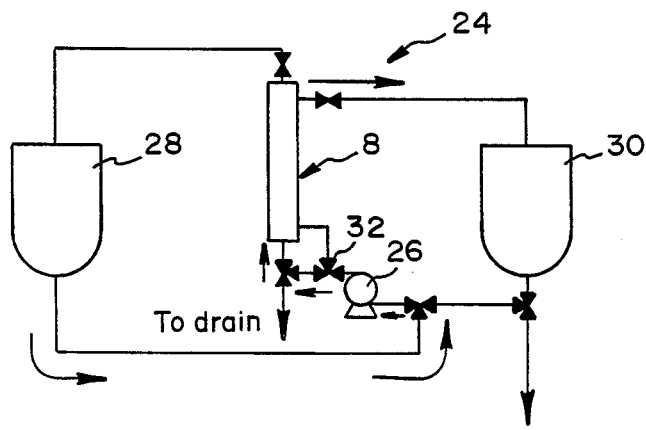
FIG. 3

LIPOSOME EXTRUSION METHOD

FIELD OF THE INVENTION

The present invention relates to methods for producing liposomes in a selected size range, preferably between about 0.1 and 0.4 microns.

REFERENCES

1. Gabizon, A., et al, Cancer Res, 43:4730 (1983).
2. Poznansky, M. L., et al, Pharm Revs, 36(4):277 (1984).
3. Szoka, F., et al, Proc Nat Acad Sci (USA), 75:4194 (1978).
4. Szoka, F., et al, Ann Rev Biophys Bioeng, 9:467 (1980).

BACKGROUND OF THE INVENTION

The use of liposomes for drug delivery has been proposed for a variety of drugs, particularly those which are administered parenterally. Liposomes have the potential for providing controlled "depot" release of the administered drug over an extended time period, and of reducing side effects of the drug, by limiting the concentration of free drug in the bloodstream. Liposomes can also alter the tissue distribution and uptake of drugs, in a therapeutically favorable way, and can increase the convenience of therapy, by allowing less frequent drug administration. Liposome drug delivery systems are reviewed in Poznansky.

Generally, the optimal liposome size for use in parenteral administration is between about 0.1 and 0.3, and up to 0.4, microns. Liposomes in this size range can be sterilized by passage through conventional filters having particle size discrimination of about 0.2 microns. This size range of liposomes also favors biodistribution in certain target organs, such as liver, spleen, and bone marrow (Gabizon), and gives more uniform and predictable drug-release rates and stability in the bloodstream. Liposomes whose sizes are less than about 0.4 microns also show less tendency to agglutinate on storage, and are thus generally safer and less toxic in parenteral use than larger-size liposomes.

A variety of techniques have been proposed for preparing liposomes, including drug-containing liposomes (Szoka 1983). Typically, these methods yield liposomes which are heterodisperse, and predominantly greater than about 1 micron in size. These initial heterodisperse suspensions can be reduced in size and size distribution by a number of known methods. One size-processing method which is suitable for large-scale production is homogenization. Here the initial heterodisperse liposome preparation is pumped under high pressure through a small orifice or reaction chamber. The suspension is usually cycled through the reaction chamber until a desired average size of liposome particles is achieved. A limitation of this method is that the liposome size distribution is typically quite broad and variable, depending on a number of process variables, such as pressure, number of homogenization cycles, and internal temperature. Also, the processed fluid has the potential to pick up metal and oil contaminants from the homogenizer pump, and may be further contaminated by residual chemical agents used to sterilize the pump seals.

Sonication, or ultrasonic irradiation, is another method that is used for reducing liposome sizes. This technique is useful especially for preparing small unilamellar vesicles (SUVs), in the 0.025–0.08 micron size range. However, a narrow size distribution of liposomes can only be achieved at liposome sizes of about 0.05 microns, i.e., when the liposomes have been substantially completely reduced in size. The very small liposomes have limited drug capacity and less favorable biodistribution properties than those in the 0.1–0.4 micron size range, as noted below. The processing capacity of this method is also quite limited, since long-term sonication of relatively small volumes is required. Also, heat build-up during sonication can lead to peroxidative damage to the lipids, and sonic probes shed titanium particles which are potentially quite toxic in vivo.

A third general size-processing method known in the prior art is based on liposome extrusion through uniform pore-size polycarbonate membranes (Szoka 1978). This procedure has advantages over the above homogenization and sonication methods in that a variety of membrane pore sizes are available for producing liposomes in different selected size ranges, and in addition, the size distribution of the liposomes can be made quite narrow, particularly by cycling the material through the selected-size filter several times. Nonetheless, the membrane extrusion method has several drawbacks in large-scale processing. For one, the pores in the membrane tend to clog, particularly when processing concentrated suspensions and/or when the liposome sizes are substantially greater than the membrane pore sizes. The clogged membranes cannot be cleared, because the filter housing configuration does not allow back flushing, and replacing the filter is likely to compromise the sterility of the extrusion operation. Secondly, the membranes themselves are planar disks which must be mounted against a flat mechanical support. This severely restricts the surface area available for extrusion, and leads to slow throughput. Although the problems of clogging and slow throughput can be overcome partially at high extrusion pressures, such requires specially adapted filter holders and membrane tearing become more of a problem. Finally, polycarbonate membranes cannot be steam-sterilized in place, with a high degree of confidence, due to their inherent fragility.

BACKGROUND OF THE INVENTION

It is therefore a general object of the invention to provide a novel liposome size-processing method which overcomes the above-mentioned limitations and problems associated with the prior art.

One specific object of the invention is to provide such a method which yields sized liposomes having a selected average size of between about 0.1 to 0.4 microns, and a relatively narrow distribution of sizes.

Still another object of the invention is to provide such a method which can be operated in a relatively problem-free manner, without heat build-up, at high throughput volumes, and in a large-scale operation.

Providing such a method which can be practiced with little risk of contamination and under sterile conditions is yet another object of the invention.

In practicing the method of the invention, a suspension of liposomes containing a substantial portion of liposomes with sizes greater than about 1 micron, are passed through an asymmetric ceramic filter having an inner-side pore size of about 1 micron. The resulting liposomes have an average particle size of between about 0.2 and 0.4 microns, depending on the number of times the liposomes are cycled through the membrane, and a standard size distribution of about 30–45%.

The suspension may be alternately passed through the membrane, in an outside-to-inside directions, to maintain the membrane in an unclogged condition, allowing high throughput processing, even for a concentrated suspension of liposomes.

The liposome average size may be further reduced by passage through similar types of ceramic filters, but which have smaller specified inner-surface pore sizes.

These and other objects and features of the present invention will become more fully apparent when the following detailed description of the invention is read in conjunction with the accompanying drawings.

BRIEF DESCRIPTION OF THE DRAWINGS

FIG. 1 is a graph showing the size distribution of multiple lamellar vesicles (MLVs) prior to size-processing according to the invention;

FIG. 2 is a sectional view of a filter apparatus of the type used in the present invention, with the inset showing an enlarged inner wall portion of a filter in the apparatus; and FIG. 3 is a flow diagram of a liposome processing system for preparing liposomes according to the present invention.

DETAILED DESCRIPTION OF THE INVENTION

I. Preparation of Liposome Suspension

A. Unsized Liposomes

The liposomes, or lipid vesicles, of the invention are formed from standard vesicle-forming lipids, which generally include neutral and negatively charged phospholipids and a sterol, such as cholesterol. A variety of lipids having selected acyl chain compositions are commercially available or may be obtained using standard lipid isolation procedures. The selection of lipids for therapeutic liposomes containing an active drug is generally guided by considerations of (a) drug-entrapment efficiency, (b) drug-release rate in serum, and (c) biodistribution and targeting properties. These considerations are discussed at length, for example, in U.S. patent application Ser. No. 806,084 for "Liposome/Anthraquinone Drug composition and Method", filed Dec. 6, 1985.

Several methods for producing a suspension of the heterogeneous-size vesicles are available. In one preferred method, vesicle-forming lipids are taken up in a suitable organic solvent or solvent system, and dried in vacuo or under an inert gas to a lipid film. Where the vesicles are formulated to include a lipophilic or amphiphilic drug, such may be included in the lipids forming the film. To form the vesicles, aqueous medium is added to the dry film, and the film is allowed to hydrate, typically over a one-two hour period with gentle shaking. The lipids hydrate to form multilamellar vesicles (MLVs) whose sizes range typically between about 0.5 microns to about 10 microns or greater. In general, the size distribution of MLVs can be shifted toward slightly smaller sizes by hydrating the lipids under more vigorous shaking conditions. The aqueous medium used in hydrating the lipid film may include a water-soluble drug which then becomes encapsulated in the vesicles which form during lipid hydration.

Example I below described describes the preparation of an MLV suspension whose size distribution is shown in FIG. 1. The lower size range of about 0.8 was the lower limit of size discrimination of the particle-sizer used. As seen, a suspension contained a broad range of sizes up to about 16 microns, with average sizes between about 2–4 microns.

For producing liposomes under conditions of high encapsulation efficiency, the reverse evaporation phase method first described by Szoka 1978 is preferred. The reverse-phase evaporation vesicles (REVs) formed by this method are characterized by (a) one or a few bilayers, (b) an encapsulation efficiency typically between about 20–50%, and (c) a broad spectrum of sizes between about 0.5 and up to 20 microns. These and other liposome-preparation methods have been reviewed extensively (Szoka 1980).

B. Sizing Liposomes

According to an important feature of the invention, the unsized liposomes are passed through an asymmetric ceramic filter, to produce liposomes with a selected average size between about 0.1 and 0.4 microns, and a narrow distribution of liposome sizes. A preferred ceramic filter is a Ceraflow TM Microfilter available commercially from the Norton Company (Worcester, MA), and supplied as a multifilter cartridge-type filter apparatus, such as seen cross-sectionally in FIG. 2. The filter apparatus 8 includes a tubular casing 10 which houses a plurality of tubular filters, such as filter 12, a side-wall portion of which is shown in enlarged view in the inset in the figure. The casing is provided with an inlet manifold (not shown) through which the liposome suspension can be supplied under pressure to the inner tubular region of each filter, such as inner region 14 of filter 12. The material, on passage through the filters, is collected from an extratubular space 16, through a casing outlet (also not shown). A useful operational feature of the filter system just described is the ability to filter in either direction, that is, in a forward, inside-to-outside direction or in a back, outside-to-inside direction in which material is pumped under pressure from the extratubular space into the filter interior regions, and collected at the casing manifold. Back direction flow may alternate with forward direction to reduce the tendency of the filters to clog.

The asymmetric construction of the filters is seen in the inset in FIG. 2, which shows an enlarged sectional view taken through a wall portion of filter 12. The filter is composed of a series of controlled-thickness ceramic layers or strata, such as layers 18, 20, and 22, arranged coaxially about the filter's inner tubular space. The layers are each composed of sintered particles, with the inner wall having the smallest particles and the outer walls having progressively larger particles. The particles forming the inner walls are dimensioned to provide a defined surface pore size in the sintered inner layer. For example, the Ceraflow TM filters supplied by Norton have surface pore sizes of either 1.0, 0.45, or 0.2 microns, and are designed for filtering particles, in a fluid flowing through the filters in an inside-to-outside direction, whose size is equal to or greater than the rated pore size.

FIG. 3 shows an extrusion system 24 employing a cartridge-type filter apparatus 8 of the type just described. The system includes a pump 26, and a pair of vessels 28, 30, which hold the liposome suspension being processed. The pump is connected to the vessels through a valving arrangement which includes a series of valves such as valve 32, for effecting fluid flow either in a forward direction (the direction of arrows in FIG.

3) from vessel 28, through the apparatus in an inside-to-outside direction, to vessel 30, or in the reverse, back direction. In an alternative system, the driving pressure is created by compressed gas which is connected to the vessels in a conventional manner. From vessel 30, the processed liposome suspension can be transferred to a sterile fill system, as indicated.

In a typical processing operation, a suspension of heterogeneous size liposomes are placed in vessel 28, and the valves are set initially to pump the suspension through the filter apparatus in a forward direction. As will be seen from the procedure described in Examples II and III, and according to an important finding of the present invention, a single passage through the 1.0 micron pore size filter apparatus reduces the average liposome size to about 0.3–0.35 microns, with a standard size deviation of about 40%. These size characteristics are suitable for purposes of subsequent filter sterilization and to desirable therapeutic properties. Alternatively, the suspension may be recycled through the filter apparatus, and preferably by alternating the flow in forward and backward directions, to reduce the average size of the liposomes selectively. For example, as described in Example II, cycling the above MLV suspension through the 1.0 pore-size filter several times gradually reduced the liposome average size from 0.3 microns (after one filtration) to about 0.2 microns (after several passes). Cycling the material alternately in a back direction acts to prevent particle build-up and clogging at the filter's inner surface.

In the filter operation described in Example III, liposome average sizes were reduced to about 0.35 microns after a single pass through a 1 micron filter and further reduced to about 0.27 microns with three passes.

If smaller liposome sizes are desired, the material can be further processed by passage through similar types of asymmetric filters having inner surface pore sizes of 0.45 or 0.2 microns. Example III shows the gradual reduction in pore size in liposomes after initial sizing using a 1 micron filter, by five passes through a 0.45 micron filter. As seen, repeated extrusion through the 0.45 micron filter reduced average liposome sizes to about 0.2 microns.

Alternatively, the material may be processed by direct passage through a smaller pore size ceramic filter (less than about 0.5 micron), to achieve direct reduction of heterogeneous-size liposomes to average sizes of about 0.2 microns or less. However, since filter clogging tends to occur when unsized liposomes are pumped through ceramic filters with smaller pore sizes, it may be necessary to increase filtration pressure, use a more dilute liposome suspension, flow the material through the filter initially in a back (outside-to-inside) direction, and/or alternate the direction of flow more frequently to achieve high-volume throughput. It is noted that smaller-pore filters are generally not needed, since direct reduction in liposome size to a size range that is suitable for parenteral use (0.2–0.3 microns) can be achieved directly, and at high throughput rates, with a 1 micron pore-size filter.

C. Filter Sterilization and Free-Drug Removal

The size-processed liposome suspension may be readily sterilized by passage through a sterilizing membrane having a particle discrimination size of about 0.2 microns, such as a conventional 0.22 micron depth membrane filter. The sterilizing filter may be an asymmetric ceramic filter of the type described above, but having an inner surface pore size of about 0.2. However, since an asymmetric filter will produce some liposome sizing effect, with the attendant possibility of higher pressure requirements and/or eventual membrane clogging, a conventional membrane filter is preferred for sterilization. Also, the tortuous path pore structure of conventional sterilizing membrane filters is preferred for maximum bacteria retention.

Where liposomes are formulated to contain an entrapped drug, for use in parenteral drug administration, it is usually advantageous to further process the sized liposomes to remove free drug, i.e., drug present in the bulk aqueous phase of the suspension. This is done to reduce the effects of free drug and to maximize the benefits achievable by drug entrapment in the liposomes. Free drug may be present in a substantial amount in the case of a water-soluble drug, which can be encapsulated at a maximum efficiency of about 50%, as noted above, or in the case of a lipophilic or amphiphilic drug which has originally been included in vesicle-forming lipids in molar excess of the liposome drug-carrying capacity, as a strategy for maximizing the drug/lipid ratio in the liposomes. It may also be desirable to reduce the bulk phase concentration of other solute molecules, such as carbohydrates, chelate agents, or the like, used in preparing the liposomes but not desired in parenteral administration.

Several methods are available for removing free drug from a liposome suspension. The sized liposome suspension can be pelleted by high-speed centrifugation, leaving free drug and very small liposomes in the supernatant. Another method involves concentrating the suspension by ultrafiltration, then resuspending the concentrated liposomes in a drug-free replacement medium. Alternatively, gel filtration can be used to separate larger liposome particles from solute (free drug) molecules. Ion-exchange chromatography may provide an efficient method of free drug removal, in instances where a suitable drug-binding resin can be identified. One preferred method of free drug removal is by diafiltration, using a conventional hollow fiber or stacked filter device, which preferably has a molecular weight cutoff of between about 10,000–100,000 daltons. Diafiltration has the advantage that it can be used in-line in a sterile liposome-processing system of the type shown in FIG. 3.

II Utility

Sized liposome suspensions prepared according to the invention are useful in a variety of liposome therapeutic compositions in which controlled sizes between about 0.1 and 0.3 microns, and within a narrow size distribution, are desired. One important class of compositions is drug-containing liposomes, for parenteral drug administration. As indicated above and reviewed extensively in the Poznansky reference, liposomal drug-delivery systems have been developed and tested with a wide range of water-soluble and lipid-soluble drugs. Although many of the earlier proposed liposome/drug systems were not carefully defined in terms of size, a variety of experimental evidence and practical considerations indicate advantages of the 0.1 to 0.3 micron size range. This size range is generally preferred to larger-size liposomes, as indicated above, because of ease of sterilization, improved biodistribution, more size uniformity, and less tendency to aggregate on storage.

With liposome sizes below about 0.1 microns, the drug-carrying capacity of the liposomes, measured either by internal encapsulation of lipid-bilayer volume, become somewhat restrictive. Also, as liposome sizes are reduced below about 0.1 microns, the liposomes appear to behave more like free drug in terms of biodistribution and drug-clearance rates. The effect of liposome size on pharmacokinetic properties of liposomes carrying the anti-tumor drug doxorubicin has been examined in connection with the drug-liposome invention described in the above mentioned U.S. patent application Ser. No. 806,084 for "Liposome/Anthraquinone Composition and Method", filed Dec. 6, 1985. As detailed there, liposomes with average sizes of about 0.035 microns were much more similar to free drug in biodistribution and drug clearance rates than liposomes with average sizes of about 0.115 microns.

The present invention offers a number of advantages over prior art liposome-sizing methods. The ceramic filter can be sterilized by dry heat at temperatures which are effective to destroy endotoxins, and the system is compatible with a variety of solvents, including many organic solvent which are not tolerated by polycarbonate-type membranes. The method generates very little heat, and can be performed under aseptic conditions.

The liposome processing method yields liposome sizes in a selected size range of between about 0.1 and 0.4 microns, and with a relatively narrow distribution of sizes i.e., uniform liposome sizes. The method is well suited to a high throughput liposome processing operation which is reliable and requires very little maintenance, such as filter cartridge replacement. High throughput is due in part to the relatively high pressure which may be used, and in part because bidirectional operation reduces clogging problems. High throughput is also due to the surface area of membrane available. A tubular cartridge configuration is more efficient in terms of membrane surface area and makes the process easily scalable.

The finding that liposomes may be directly and efficiently reduced from heterogeneous sizes predominantly greater than 1 micron, to a narrow distribution of sizes in a selected size range between about 0.2 and 0.3 microns, using a filter with an inner-wall pore size of 1 micron, allows for direct liposome sizing without the need to pass the liposome suspension through a series of progressively smaller pore-size membranes, as has been generally found for polycarbonate membranes.

The following examples illustrate both use and results achievable with the method of the invention, but are in no way intended to limit the scope of the invention.

EXAMPLE I

Preparation of Heterogeneous-Size Liposomes

Phosphatidylcholine (PC) was obtained from Asahi Lipids (Japan), cholesterol (CH) from Sigma Chemical Co. (St. Louis, MO), and phosphatidylglycerol (PG) were obtained from Avanti Lipid (Birmingham, AL). PC (0.12 moles), CH (0.09 moles), and PG (0.01 moles) were dissolved in 260 ml of chloroform, and the solvent was removed by rotary evaporation under reduced pressure, leaving a thin film of lipid in the flask. One liter of hydration buffer consisting of 10.7 mM $NaH_2PO_4.H_2O$, 48.4 mM $Na_2HPO_4.7H_2O$, pH 7.4, and 86.1 mM NaCl was added to the flask and swirled gently over the lipids. The lipids were allowed to swell gently for about 2 hours.

The size distribution of a typical suspension made as described above was measured in a Coulter Counter, Model TA2, using a 50 micron aperture tube. The counter device is capable of discriminating size between about 0.8 and 20 microns, and is programmed to express each size window as a percentage of volume distribution, based on a 100% volume distribution in the 0.8–20 micron size range. The size-distribution curves for the liposomes are shown in FIG. 1. It is noted that only those liposomes whose sizes are more than about 0.8 microns are included in the normalized curves. That is, the size distribution curves do not show actual volume percentages below 0.8 micron sizes. As seen, the liposomes have a broad distribution over the size range 0.8 to greater than 16 microns, with an average size of between about 2–4 microns.

EXAMPLE II

Liposome Size Processing

An asymmetric ceramic filter apparatus having a specified inner surface pore size of 1.0 micron was obtained from the Norton Company (Worcester, MA). The filter was connected in a two-vessel system of the type shown in FIG. 3, but using a pressurized nitrogen supply source to pump fluid from one vessel to the other through the filter apparatus.

The liposome suspension from Example I was added to the first vessel, and the vessel was pressurized with filtered nitrogen gas to about 200–250 psi. The valve arrangement connecting the two vessels was first adjusted to pump the suspension through the filter apparatus, in a forward, inside-to-outside direction, into the second vessel. The valving in the system was then reversed to pump the suspension through the filter apparatus in a back direction. The material was filtered an additional eight times, four times in a forward direction and four times alternately in a back direction, with sample material being removed after each step for later size-distribution determination.

The size distribution of the liposomes for each of the ten samples was determined using a conventional particle sizer calibrated with latex particle size standards. From the measured sizes of the sample, the machine calculates mean particle diameter and percent standard deviation with respect to the mean values. The data are shown in Table 1 below. Odd number passes were in a forward direction through the filter apparatus, and even number passes were in a back direction.

TABLE 1

| No. of Passes* | Mean Diam. (nm) | Std. Dev. (%) |
|---|---|---|
| 1 | 301.4 | 36.5 |
| 2 | 300.7 | 38.1 |
| 3 | 259.4 | 32.6 |
| 4 | 251.8 | 36.2 |
| 5 | 239.7 | 34.2 |
| 6 | 241.8 | 33.4 |
| 7 | 233.1 | 33.6 |
| 8 | 234.6 | 31.1 |
| 9 | 233.2 | 33.4 |
| 10 | 223.5 | 35.1 |

The data show a gradual reduction in average liposome size, with increasing filtration steps, from about 0.3 to 0.2 microns. The extent of size reduction produced by each filtration step appears to be greater in the forward direction than in the back direction. Interestingly, the standard deviation of sizes was not improved appreciably by repeated passages through the filter.

EXAMPLE III

Liposome Size Processing

The liposome suspension from Example I was added to one vessel in a two-vessel system of the type shown in FIG. 3, and the valve arrangement connecting the two vessels was adjusted to pump the suspension through a 1 micron ceramic filter apparatus (Example II), in a forward, inside-to-outside direction, into the second vessel. The valving in the system was then reversed to pump the suspension through the filter apparatus in a back direction. The material was passed through the filter a third time in a forward direction. The $1\mu$ filter was then replace with a $0.45\mu$ ceramic filter (Norton Company) and the material pumped through the apparatus three times in a forward direction (passes 4, 6, and 8) and two times in a back direction (passes 5 and 7). The size distribution of the liposomes after each pass was determined as in Example II. The data are shown in Table 2 below, along with the gauge pressure, in psi, used at each pass.

TABLE 2

| No. of Passes | Filter Size | Pressure (psi) | Mean Diam. (nm) | Stan. Dev. (%) |
|---|---|---|---|---|
| 1 | $1\mu$ | 400 | 344.3 | 42 |
| 2 | $1\mu$ | 75 | 295.8 | 35 |
| 3 | $1\mu$ | 250 | 269.2 | 35 |
| 4 | $0.45\mu$ | 150 | 234.0 | 33 |
| 5 | $0.45\mu$ | 75 | 242.0 | 32 |
| 6 | $0.45\mu$ | 250 | 215.1 | 31 |
| 7 | $0.45\mu$ | 70 | 210.9 | 31 |
| 8 | $0.45\mu$ | 150 | 210.4 | 29 |

The data show a gradual reduction in average liposome size, with increasing filtration steps, from about 0.35 to 0.2 microns. The gradual reduction in size, after replacing the 1 micron filter with a 0.45 micron filter, is not significantly greater than that achieved in Example II using a 1 micron filter only. The data also show that the required filtration pressure was substantially greater in the forward than in the back direction.

While preferred embodiments of the invention have been described herein, it will be apparent to those skilled in the art that various changes and modifications can be made without departing from the invention.

It is claimed:

1. A method of producing a suspension of liposomes which have uniform sizes and a selected average size of less than about 0.4 microns, said method comprising:
   providing a suspension of heterogeneous-size liposomes containing a substantial portion with sizes greater than 1.0 micron in size, and
   passing the suspension under pressure through an asymmetric ceramic filter whose inner-surface pore size is greater than the desired average liposome size and no greater than about 1 micron.

2. The method of claim 1, wherein the liposome suspension is passed through the filter in an inside-to-outside direction.

3. The method of claim 1 wherein the membrane is a Ceraflow TM asymmetric ceramic filter.

4. The method of claim 1, for producing a suspension of liposomes having a selected average size of between about 0.3 and 0.4 microns, wherein said asymmetric filter has an inner-surface pore size of about 1 micron.

5. The method of claim 1, for producing a suspension of liposomes having a selected average size of between about 0.2 and 0.3 microns, wherein said asymmetric filter has an inner-surface pore size of about 0.45 microns in size.

6. The method of claim 5, for producing a suspension of liposome having a selected average size between about 0.2 and 0.3 microns, which further includes passing the suspension repeatedly through the filter, in an inside-to-outside direction, until the desired liposome average size is achieved.

7. The method of claim 6 which further includes alternately passing the suspension through the filter in an outside-to-inside direction.

* * * * *